United States Patent [19]

Marosi et al.

[11] 4,401,637
[45] Aug. 30, 1983

[54] CRYSTALLINE ISOTACTIC ZEOLITES AND THEIR PREPARATION

[75] Inventors: Laszlo Marosi, Ludwigshafen; Joachim Stabenow, Weinheim; Matthias Schwarzmann, Limburgerhof, all of Fed. Rep. of Germany

[73] Assignee: BASF Aktiengesellschaft, Fed. Rep. of Germany

[21] Appl. No.: 234,925

[22] Filed: Feb. 17, 1981

[30] Foreign Application Priority Data

Feb. 21, 1980 [DE] Fed. Rep. of Germany ....... 3006471

[51] Int. Cl.$^3$ .................... C01B 33/28; C07F 5/06; B01D 29/16
[52] U.S. Cl. .................... 423/329; 260/448 A; 260/448 C; 423/328; 252/431 N; 252/455 Z
[58] Field of Search .................... 252/431 N, 455 Z; 260/448 A, 448 C; 423/328, 328 T, 329, 329 T

[56] References Cited

U.S. PATENT DOCUMENTS

| | | | |
|---|---|---|---|
| 3,702,336 | 11/1972 | Argauer et al. | 260/448 C |
| 4,025,571 | 5/1977 | Lago | 585/640 |
| 4,049,573 | 9/1977 | Kaeding | 585/640 |
| 4,091,007 | 5/1978 | Dwyer et al. | 423/118 |
| 4,107,195 | 8/1978 | Rollmann | 260/448 C |
| 4,108,881 | 8/1978 | Rollmann et al. | 423/328 |
| 4,134,600 | 2/1979 | Rollmann et al. | 260/448 C |
| 4,151,189 | 4/1979 | Rubin et al. | 260/448 C |
| 4,259,537 | 3/1981 | Chu | 585/475 X |
| 4,299,732 | 11/1981 | Bell et al. | 423/328 X |

FOREIGN PATENT DOCUMENTS

| | | | |
|---|---|---|---|
| 7081 | 1/1980 | European Pat. Off. | 423/329 |
| 2442240 | 3/1975 | Fed. Rep. of Germany . | |
| 2817575 | 10/1978 | Fed. Rep. of Germany . | |
| 2817576 | 11/1978 | Fed. Rep. of Germany . | |
| 2066230 | 7/1981 | United Kingdom | 423/329 |

OTHER PUBLICATIONS

*The Merck Index,* 8th Ed., Merck & Co., Inc.; Rahway, N.J. 1968, pp. 529 & 794.

*Primary Examiner*—Delbert E. Gantz
*Assistant Examiner*—Raymond Covington
*Attorney, Agent, or Firm*—Keil & Witherspoon

[57] ABSTRACT

Crystalline isotactic zeolites having the composition

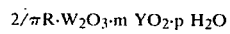
$2/n R \cdot W_2O_3 \cdot m \, YO_2 \cdot p \, H_2O$ where R is an organic amine and n is the number of amine groups in the amine molecule, W is one or more of the elements B, Al, Ga and Fe and Y is Si and/or Ge, and a process for the preparation of these crystalline isotactic metal silicate zeolites from mixtures of $YO_2$ and $W(OH)_3$ by hydrothermal crystallization at from 100° to 200° C. with the aid of an organic amine, in the absence of an alkali metal base, alkaline earth metal base or quaternary nitrogen base or their intermediates, the number m depending on the chain length of the organic amine used in the crystallization.

11 Claims, No Drawings

CRYSTALLINE ISOTACTIC ZEOLITES AND THEIR PREPARATION

The present invention relates to novel zeolites, a process for their preparation, and the use of these zeolites as catalysts.

Zeolites of the A, X, Y and mordenite type have become very important industrially. They are used industrially as ion exchangers, molecular sieves and catalysts. Processes employing zeolite catalysts include catalytic cracking and hydro-cracking of hydrocarbons. At the present time, there is increasing interest in zeolites of the ZSM-5 type for such reactions as, for example, the conversion of methanol to aromatics and/or olefins.

Zeolites are crystalline silicates, especially aluminosilicates. They are prepared by hydrothermal crystallization of reactive $SiO_2$ and $Al_2O_3$ starting materials in the presence of a strong base. This base may be an alkali metal hydroxide, alkaline earth metal hydroxide, or quaternary nitrogen base or phosphorus base, or a mixture of these. The disadvantages of the known methods synthesis are that the quaternary nitrogen base used is difficult to obtain, and that the alkali metal cation must be replaced by other cations so as to arrive at the catalytically active form. The use of a primary amine or diamine in conjunction with alkali metal ions, in place of quaternary nitrogen bases, produces some simplification of the preparation of zeolites of the ZSM-5 type. These conventional processes are described, for example, in German Laid-Open Applications DOS 2,442,240, DOS Nos. 2,817,575 and DOS Nos. 2,817,576. A feature of all these processes is that the synthesis is carried out in the presence of alkali metal ions or alkaline earth metal ions and that hence the zeolites obtained also contain alkali metal ions. Other processes, which are carried out in the absence of alkali metal ions, employ quaternary nitrogen bases, which are to be regarded as strong bases, for the crystallization.

The present invention relates to novel crystalline isotactic zeolites of the composition $$(2/n) R.W_2O_3.m\ YO_2.p\ H_2O$$

where R is an organic amine and n is the number of amine groups in the amine molecule, W comprises the elements B, Al, Ga and Fe, Y comprises the elements Si and Ge, and m is $$m = (1 \pm 0.15)\frac{96 - \frac{40n}{L_R + K}}{\frac{20n}{L_R + K}}$$

where $L_R$ is the length of the amine molecule in Å, K is a constant having a value of about 4, p is a number from 0 to 160 and the crystalline isotactic zeolite material exhibits X-ray diffraction lines corresponding to one or more of the following spacings:

$$d(\text{Å}) = 11.1 \pm 0.3/10.0 \pm 0.25/3.85 \pm 0.1/3.71 \pm 0.1/3.54 \pm 0.07$$

The isotactic zeolites according to the invention are obtained by hydrothermal treatment of a mixture of $W_2O_3$ and $YO_2$ in the presence of an organic amine for from 1 to 15 days at from 100° to 200° C., the ratio $YO_2/W_2O_3$ being so chosen that the crystalline isotactic zeolite has the composition corresponding to the formula $$(2/n) R.W_2O_3.m\ YO_2.p\ H_2O.$$

Advantageously, only as much $W_2O_3$ as is needed to form the crystalline isotactic zeolite is added. If $Al_2O_3$ is added, the amount added corresponds to the calculated quantity. Boric acid, on the other hand, is water-soluble, unlike $Al(OH)_3$. Hence, it is advantageous to use a lower $SiO_2/B_2O_3$ ratio in the reaction mixture than corresponds to the composition of the crystalline zeolite.

Further, we have found that the novel zeolites are particularly suitable for use as catalysts for the conversion of alcohols and/or dialkyl ethers to olefins and/or aromatics.

It is surprising that these novel zeolites having special properties are obtained in the absence of a strong base, by carrying out the hydrothermal crystallization with the aid of substantially less basic organic amines.

The zeolites resulting from the process according to the invention exhibit special properties, in respect of which they differ from conventional zeolites, for example from those prepared with the aid of an alkali or quaternary nitrogen base, even if the products are of the same structural type. Zeolites having the properties of the novel products cannot be obtained from conventional types of zeolite, either by ion exchange or by other modifications, nor can they be synthesized directly by conventional methods of preparation. The novel properties result from the composition according to the invention, which in turn is achieved through a specific composition of the reaction mixture, chosen in accordance with the chain length of the amine used for the crystallization.

The process according to the invention is carried out in the presence of organic amines which have a substantially lower basicity than that of an alkali or of a quaternary nitrogen base, for example a primary or secondary amine, such as dipropylenetriamine, dihexamethylenetriamine, hexamethylenediamine, propylenediamine, diethylenetriamine or triethylenetetramine, or in the presence of a mixture of such amines.

The special properties of these novel zeolite materials are attributable to an ordered (isotactic) arrangement of the trivalent metal atoms, for example the aluminum atoms in the lattice, which arrangement differs from that of the conventional zeolites of the same structural type, prepared in the presence of an alkali or of a quaternary nitrogen base or phosphorus base. The noval zeolites have a characteristic lower limit of the $SiO_2/W_2O_3$ molar ratio, which depends on the chain length of the amine used, and on the number of amino groups in the molecule.

If, for example, $SiO_2/Al(OH)_3$ mixtures are crystallized in the presence of hexamethylenediamine under the above conditions, zeolites hereafter referred to as ZBM-10 are obtained, which have a structure similar to the conventional zeolites ZSM-5, ZSM-8 and ZSM-11, but can be unambiguously distinguished from these by X-ray diffraction analysis.

In particular, it has been found that, for example, the $SiO_2/Al(OH)_3$ mixtures can be caused to crystallize with the aid of hexamethylenediamine only if the $SiO_2/Al_2O_3$ molar ratio is not less than about 33. If, on the other hand, attempts are made to crystallize $SiO_2/Al$-

(OH)₃ mixtures, having an $SiO_2/Al_2O_3$ molar ratio of about 10-20, with the aid of hexamethylenediamine at from 150° to 190° C. in the absence of an alkali and of a quaternary nitrogen base, substantially amorphous products are obtained. The said mixtures give crystalline zeolites only if they contain a strong base.

This result is surprising since it is known that using the conventional processes zeolites of the ZSM-5 type can be prepared with $SiO_2/Al_2O_3$ molar ratios from about 5 upward, even if the crystallization is carried out with the aid of hexamethylenediamine in the presence of an alkali.

The relation between chain length of the amine, number of amine groups in the amine molecule, and maximum aluminum content in the zeolite crystal also applies when using other weakly basic amines. At the same time the $YO_2/W_2O_3$ ratios vary in a characteristic manner in accordance with the above formula.

Table 1 below shows the relation between chain length of the amine used and maximum content of aluminum in the crystal lattice, in the form of the results of crystallization experiments.

TABLE 1

| R | $L_R$ (Å) | $96 - \frac{40n}{L_R + 4}$ $\frac{20n}{L_R + 4}$ | $SiO_2/Al_2O_3$ molar ratio | Product |
|---|---|---|---|---|
| Dipropylene-triamine | 12.0 | 23.6 | 23 | amorphous |
|  |  |  | 26 | crystalline |
| Hexamethylene-diamine | 10.7 | 33.3 | 30 | amorphous |
|  |  |  | 33 | crystalline |
|  |  |  | 35 | crystalline |
| Dihexamethylene-triamine | 20.0 | 36.4 | 33 | amorphous |
|  |  |  | 38 | crystalline |
| Triethylene-tetramine | 13.4 | 18.9 | 19 | crystalline |
|  |  |  | 15 | amorphous |
| Propylenediamine | 6.7 | 23.7 | 22 | crystalline |
| Diethylenetri-amine | 9.4 | 19.4 | 20 | crystalline |
|  |  |  | 15 | amorphous |

The experiments in the Table substantiate the relation between the special properties of these zeolites and the special structure. The spacing between, for example, two aluminum atoms in the crystal lattice of the zeolite is dependent on the distance between the amino groups of the amine molecule and repeats at periodic intervals.

The catalytic activity of the novel zeolites, prepared in the presence of various amines, was tested, inter alia, for the conversion of methanol to hydrocarbons.

We found that zeolite ZBM-10 ($SiO_2/Al_2O_3=33$), used for the conversion of a methanol-water mixture in the molar ratio of 1:5, predominantly gives olefins, whilst ZBM-11, a zeolite prepared using boric acid instead of Al(OH)₃, and hexamethylenediamine, and ZBM-12, a zeolite prepared using aluminum hydroxide and dipropylenetriamine, for the same ratio of 33 of $SiO_2/B_2O_3$ and $SiO_2/Al_2O_3$, respectively, convert concentrated methanol solutions (of 85–100% strength) predominantly to propylene (ZBM-11), and predominantly to ethylene and propylene (ZBM-12). Under the same reaction conditions, zeolite ZBM-10, employed on 95% strength methanol, gave predominantly liquid hydrocarbons.

These results demonstrate that it is possible to prepare zeolites of the aluminosilicate, borosilicate or iron silicate type, or of a type comprising mixed crystals of these, which zeolites convert methanol to different products depending on the catalysts used, under otherwise identical reaction conditions and without any additional measure; for example, different catalysts of this type can convert methanol to a mixture of ethylene and propylene, or to a mixture consisting predominantly of propylene, or to a mixture of liquid hydrocarbons.

The use of the novel zeolites as catalysts offers great technological advantages over the use of conventional zeolites, namely:

(a) pure methanol or crude methanol can, without any further measure, be converted to olefins, and even for 100% conversion the throughput can be as much as 10 g of methanol/g of zeolite/h and (b) the catalysts, for example zeolite ZBM-11, carbonize more slowly than do comparable conventional zeolites.

The novel zeolites differ from other, conventional types of the ZSM-5 family not only in respect of their special composition, resulting from their special method of preparation. For example, zeolite ZBM-11 differs from other ZSM-5 types in that it is free from alkali metal and/or free from quaternary nitrogen bases and that its X-ray diffraction diagram differs unambiguously from that of other, conventional metal silicates of similar structural type. A particularly characteristic feature is the shift of the X-ray diffraction lines to smaller d values than are found, for example, with X-zeolites and Y-zeolites or the $SiO_2$ modification derivable therefrom and having a faujasite structure, and, for example, the absence of the relatively intense diffraction lines at d=4.27 Å, if HMD is used for the crystallization.

The novel zeolites can be prepared, for example, by crystallizing mixtures of reactive $SiO_2$, such as pyrogenic silica (Aerosil) and active aluminum oxide, for example using freshly precipitated Al(OH)₃, B(OH)₃ or Fe(OH)₃, under hydrothermal conditions, in the presence of an organic amine. Suitable crystallizing agents are all amines (other than quaternary nitrogen bases or their intermediates), having a chain length of not less than about 6 Å.

A particular embodiment of the preparation of the novel alkali-free zeolites consists in, for example, preparing a reaction mixture of $SiO_2$ and aluminum oxide or hydroxide, or their sodium-free intermediates, in the above ratio and then heating this mixture, in an aqueous amine solution, for from 2 hours to 8 days at from 100° to 200° C., preferably from 1 to 4 days at from 140° to 170° C., under autogeneous pressure. The zeolites thus prepared as a rule contain substantial amounts of the amine used, occluded in the intra-crystalline pores. This amine can be removed from the pores, for example by combustion, the catalytically active hydrogen form being produced thereby.

It is an advantageous feature that the mother liquor can be entirely re-used to prepare fresh zeolite.

EXAMPLE 1

101 g of Aerosil, and Al(OH)₃ freshly precipitated from 49 g of Al(NO₃)₃.9 H₂O by means of ammonia, are introduced into 1,200 g of 50% strength dipropylenetriamine solution. The mixture is then stirred until it is homogeneous, after which it is heated for 7 days at 170° C. in a steel autoclave. The crystalline product is filtered off, washed and dried at 100° C. According to X-ray (diffraction) analysis, it consists of a well-crystallized aluminum zeolite of the pentasil type.

EXAMPLE 2

Mixtures of $SiO_2$ and Al(OH)₃ are prepared and, using the method described in Example 1, an amount equivalent to 101 g of SiO₂ plus the amount of Al(OH)₃ corresponding to the particular SiO₂/Al₂O₃ molar ratio is treated hydrothermally in 1,200 g of 50% strength amine solution for 7 days at 170° C. The composition of the reaction mixture, the crystallization conditions and the results of the experiments are summarized in Table 2.

TABLE 2

| R | Molar ratio SiO₂/Al₂O₃ | Product |
| --- | --- | --- |
| Dipropylenetriamine | 23 | amorphous |
|  | 26 | crystalline |
| Hexamethylenediamine | 30 | amorphous |
|  | 35 | crystalline |
| Dihexamethylenetriamine | 33 | amorphous |
|  | 38 | crystalline |
| Propylenediamine | 22 | crystalline |
| Triethylenetriamine | 19 | crystalline |
|  | 15 | amorphous |
| Diethylenetriamine | 20 | crystalline |
|  | 15 | amorphous |

EXAMPLE 3

In each case, 2,000 g of 50% strength hexamethylenediamine solution are used, and 160 g of Aerosil are introduced, together with 40 g of boric acid in experiment (a) and 30.4 g of boric acid in experiment (b). The mixture is in each case stirred until homogeneous and then heated for 5 days in a steel autoclave at 150° C. The products are filtered off, washed and dried. According to X-ray diffraction analysis, product (a) is amorphous, whilst product (b) consists of well-crystallized boron zeolite; the SiO₂/B₂O₃ ratio in product (b) is 33. The experiment shows that the maximum boron content which gives a crystalline zeolite corresponds to an SiO₂/B₂O₃ ratio of about 33.

EXAMPLE 4

100 g of the zeolite obtained in Example 3b are converted, together with boehmite, to extrudates 1 mm in diameter; these contain 65% by weight of zeolite. 20 g of the product obtained are fitted, as the catalyst, into a continuous-flow reactor, and the activity of the catalyst in various reactions is tested.

Preparation of olefins from methanol

Crude methanol containing 17% by weight of water is passed over the catalyst at 380° C. The throughput is 10 g of crude methanol per hour per g of catalyst. The reaction conditions are as follows:

| Entry temperature | 380° C. |
| --- | --- |
| Pressure | 1.16 bar |
| Temperature rise | 220° C. |
| Conversion | 100% |

The reaction product obtained is composed of 22% by weight of liquid hydrocarbons and 78% by weight of gaseous reaction products, based on —CH₂— employed.

The gaseous products consist of 5.6% by volume of CH₄, 24% by volume of C₂H₄, 3.7% by volume of C₃H₈, 42% by volume of C₃H₆, 5.6% by volume of butane and 20.3% by volume of butenes.

EXAMPLE 5

20 g of dimethyl ether per hour are passed over 20 g of a catalyst obtained as described in Example 3b.

| Entry temperature | 330° C. |
| --- | --- |
| Temperature rise | 120° C. |
| Throughput | 1 g of dimethyl ether per g of catalyst per hour |

66% by weight of —CH₂— of liquid hydrocarbons are obtained, consisting of 38% by weight of aromatics, 38.5% by weight of aliphatics and 23.5% by weight of liquid olefins.

EXAMPLE 6

A C₄ cut is reacted over a catalyst prepared as described in Example 3b, the entry temperature being 360–370° C. and the throughput 2 g of C₄ cut per g of catalyst per hour.

The reaction products contain 67% by weight of liquid hydrocarbons, which consist of 75% of aromatics, 21% of aliphatics and 4% of olefins.

We claim:

1. A process for the preparation of a crystalline isotactic zeolite of the composition $$2/nR \cdot W_2O_3 \cdot mYO_2 \cdot PH_2O$$

where R is an organic amine having a lower basicity than that of an alkali base or of a quaternary nitrogen base and n is the number of amine groups in the amine molecule, W is selected from the group comprising B, Al, Ga, Fe or any combination thereof, Y is selected from the group comprising Si, Ge or any combination thereof, and m is $$m = (1 \pm 0.15) \frac{96 - \frac{40n}{L_R + K}}{\frac{20n}{L_R + K}}$$

where $L_R$ is the length of the amine molecule in Å, K is a constant having a value of 4, p is a number of from 0 to 160 and the crystalline isotactic zeolite material exhibits one or more of the following diffraction lines d(Å)=11.1±0.3/10.0±0.25/3.85±0.1/3.71±0.1/3.54-±0.07 from a mixture of YO₂ and W₂O₃ by hydrothermal crystallization at from 100 to 200° C., wherein the crystallization is carried out in the absence of an alkali metal base, alkaline earth metal base and quaternary nitrogen base and their intermediates, with the aid of an organic amine, the molar ratio of YO₂ to W₂O₃ in the reaction mixture being brought to a value, depending on the chain length $L_R$ of the organic amine, which is appropriate for the formation of the isotactic zeolite, the molar ratio H₂O/amine being from 0.4 to 100 and molar ratio amine/Al₂O₃ being from 5 to 400.

2. A crystalline isotactic zeolite, prepared in the absence of an alkali metal base, alkaline earth metal base and quaternary nitrogen base and their intermediates according to the process of claim 1, of the composition $$2/nR \cdot W_2O_3 \cdot mYO_2 \cdot PH_2O$$

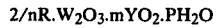

where R is an organic amine having a lower basicity than that of an alkali base or of a quaternary nitrogen base and n is the number of amine groups in the amine molecule, W is selected from the group comprising B, Al, Ga, Fe, or any combination thereof, Y is selected from the group comprising Si, Ge, or combination thereof, and m is $$m = (1 \pm 0.15) \frac{96 - \frac{40n}{L_R + K}}{\frac{20n}{L_R + K}}$$

where $L_R$ is the length of the amine molecule in A, K is a constant having a value of 4, p is a number from 0 to 160 and the crystalline isotactic zeolite material exhibits one or more of the following diffraction lines d(A)=11.1±0.3/10.0±0.25/3.85±0.1/3.71±0.1/3.54-±0.07.

3. A process for the preparation of a crystalline isotactic aluminosilicate zeolite as claimed in claim 1 from a mixture of SiO$_2$ and Al(OH)$_3$, by hydrothermal crystallization at from 100° to 200° C., wherein the crystallization is carried out in the absence of alkali metal bases, alkaline earth metal bases or quaternary nitrogen bases or their intermediates, with the aid of an organic amine, and using, in the reaction mixture, a molar ratio SiO$_2$/Al$_2$O$_3$ which depends on the chain length $L_R$ of the organic amine and is given by $$SiO_2/Al_2O_3 = (1 \pm 0.15) \frac{96 - \frac{40n}{L_R + 4}}{\frac{20n}{L_R + 4}}$$

the molar ratio H$_2$O/amine being from 0.4 to 100 and the molar ratio amine/Al$_2$O$_3$ being from 5 to 400.

4. A process for the preparation of a crystalline isotactic borosilicate zeolite as claimed in claim 1 from a mixture of SiO$_2$ and B(OH)$_3$, by hydrothermal crystallization at from 100 to 200° C., wherein the crystallization is carried out in the absence of alkali metal bases, alkaline earth metal bases or quaternary nitrogen bases or of their intermediates, with the aid of organic amines, and only as much B(OH)$_3$ is added to the reaction mixture as is required for the formation of the crystalline, isotactic borosillicate zeolite.

5. A process as claimed in claim 2, wherein the hydrothermal crystallization is carried out with hexamethylenediamine.

6. A process as claimed in claim 2, wherein the hydrothermal crystallization is carried out with dipropylenetriamine.

7. A process as claimed in claim 2, wherein the hydrothermal crystallization is carried out with propylenediamine.

8. A process as claimed in claim 2, wherein the hydrothermal crystallization is carried out with dihexamethylenetriamine.

9. A process as claimed in claim 2, wherein the hydrothermal crystallization is carried out with triethylenetetramine.

10. A process as claimed in claim 2, wherein the hydrothermal crystallization is carried out with diethylenetriamine.

11. A process for the preparation of a crystalline isotactic zeolite as claimed in claim 2, wherein the H form of the zeolite is obtained by removing the amine component.

* * * * *

UNITED STATES PATENT AND TRADEMARK OFFICE
CERTIFICATE OF CORRECTION

PATENT NO. : 4,401,637
DATED : August 30, 1983
INVENTOR(S) : Laszlo MAROSI et al.

It is certified that error appears in the above-identified patent and that said Letters Patent is hereby corrected as shown below:

IN THE CLAIMS:

Claim 1, column 6, lines 28 and 64, the last four letters of the formula should read "$pH_2O$" and not "$PH_2O$".

Signed and Sealed this

Twenty-eighth Day of February 1984

[SEAL]

Attest:

GERALD J. MOSSINGHOFF

Attesting Officer  Commissioner of Patents and Trademarks